US006991795B1

(12) United States Patent
Lowe et al.

(10) Patent No.: US 6,991,795 B1
(45) Date of Patent: Jan. 31, 2006

(54) PROTEIN DELIVERY SYSTEM USING HUMAN PAPILLOMAVIRUS VIRUS-LIKE PARTICLES

(75) Inventors: Robert S. Lowe, North Wales, PA (US); Kathrin U. Jansen, Doylestown, PA (US); Joseph G. Joyce, Lansdale, PA (US); William L. McClements, Doylestown, PA (US); James C. Cook, III, Lansdale, PA (US); Jessica Ching-Yee Ling, Bensalem, PA (US); Michael P. Neeper, Collegeville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/762,794

(22) PCT Filed: Aug. 10, 1999

(86) PCT No.: PCT/US99/17931

§ 371 (c)(1),
(2), (4) Date: Mar. 23, 2001

(87) PCT Pub. No.: WO00/09157

PCT Pub. Date: Feb. 24, 2000

Related U.S. Application Data (60) Provisional application No. 60/096,638, filed on Aug. 14, 1998.

(51) Int. Cl.
C12N 7/04 (2006.01)
C07K 14/025 (2006.01)
A61K 39/12 (2006.01)

(52) U.S. Cl. .............. 424/185.1; 424/186.1; 424/192.1; 424/204.1; 435/455; 435/456; 435/320.1; 435/325; 435/366; 435/371; 536/23.1; 536/23.72; 514/2

(58) Field of Classification Search ............... 435/455, 435/456, 320.1, 325, 366, 371; 536/23.1, 536/23.72; 514/2, 44; 424/185.1, 186.1, 424/192.1, 204.1
See application file for complete search history.

(56) References Cited

U.S. PATENT DOCUMENTS

| 5,437,951 A | | 8/1995 | Lowy et al. |
| 5,618,536 A | | 4/1997 | Lowy et al. |
| 5,855,891 A | * | 1/1999 | Lowy et al. .............. 424/192.1 |
| 6,066,324 A | * | 5/2000 | Gissmann et al. ....... 424/204.1 |
| 6,352,696 B1 | | 3/2002 | Hallek et al. |

FOREIGN PATENT DOCUMENTS

WO WO 96/11272 * 4/1996

OTHER PUBLICATIONS

Philip K. Nicholls et al, The Immunology of animal papillomaviruses, Veterinary Immunology and Immunopathology 73, 2000, 101-127.*
Cohen, Bumps on the Vaccine Road, Science vol. 265, Sep. 1994.*
Heather L. Greenstone et al. Chimeric papillomavirus virus-like particles elicit antitumor immunity against the E7 oncoprotein in an HPV16 tumor model, vol. 95, pp. 1800-1805, Feb. 1998.*
Greenstone, H. et al. "Chimeric papillomavirus virus-like particles elicit antitumor immunity against the E7 oncoprotein in an HPV16 tumor model", Proc. Natl. Acad. Sci. USA, 1998, vol. 95, pp. 1800-1805.
Peng, S. et al. "Papillomavirus Virus-like Particles Can Deliver Defined CTL Epitopes to the MHC Class I Pathway", Virology, 1998, vol. 240, pp. 147-157.
Schafer, K. et al. "Immune Response to Human Papillomavirus 16 L1E7 Chimeric Virus-Like Particles: Induction of Cytotoxic T Cells and Specific Tumor Protection", Int. J. Cancer, 1999, vol. 81, pp. 881-888.

* cited by examiner

*Primary Examiner*—David Guzo
(74) *Attorney, Agent, or Firm*—Alysia A. Finnegan; Joanne M. Giesser (57) ABSTRACT

Human Papillomavirus virus like particles (VLPs) have been constructed so that they contain a modified L2 protein. The L2 protein has been minimized and is fused to a second protein or peptide. The fused protein is incorporated into the VLP and the VLP can deliver the protein to a cell. The modified VLPs can be used to increase the breadth of immune response in vaccine preparations or to deliver other proteins of interest.

5 Claims, 4 Drawing Sheets

```
                                                    Sma I
                    primer I (SEQ ID NO:1)  >cttcccccgggcacaaaacaaa
                                             cttcccccgggcacaaaacaaa
atgc>
ATGcgacacaaacgttctgcaaaacgcacaaaacgtgcatcggctacccaactttataaa
acatgcaaacaggcaggtacatgtccacctgacattatacctaaggttgaaggcaaaact
attgctgatcaaatattacaatatggaagtatgggtgtattttttggtgggttaggaatt
ggaacagggtcgggtacaggcggacgcactgggtatattccattgggaacaaggcctccc
                                                           (SEQ ID NO:9)
        <cccagcccatgtccgccGgcgCTCGAGCTC<   primer C
         (SEQ ID NO:14)      Not I     Sac I
                                       Xho I acagctacagatacacttgctcctgtaagaccccctttaacagtagatcctgtgggccct
tctgatccttctatagtttctttagtggaagaaactagttttattgatgctggtgcacca
acatctgtaccttccatcccccagatgtatcaggatttagtattactacttcaactgat
accacacctgctatattagatattaataatactgttactactgttactacacataataat
cccactttcactgacccatctgtattgcagcctccaacacctgcagaaactggagggcat
tttacactttcatcatccactattagtacacataattatgaagaaattcctatggataca
tttattgttagcacaaacccctaacacagtaactagtagcacacccataccagggtctcgc
ccagtggcacgcctaggattatatagtcgcacaacacaacaagttaaagttgtagaccct
gcttttgtaaccactcccactaaacttattacatatgataatcctgcatatgaaggtata
gatgtggataatacattatattttcctagtaatgataatagtattaatatagctccagat
cctgactttttggatatagttgctttacataggccagcattaacctctaggcgtactggc
attaggtacagtagaattggtaataaacaaacactacgtactcgtagtggaaaatctata
ggtgctaaggtacattattattatgatttgagtactattgatcctgcagaagaaatagaa
ttacaaactataacaccttctacatatactaccacttcacatgcagcctcacctacttct
attaataatggcttatatgatatttatgcagatgactttattacagatacttctacaacc
(SEQ ID NO:10)
                  Not I     Sac I
                            Xho I
primer A  >GCGGCCGCGAGCTCGAGggttatattcctgcaaatacaac>
(SEQ ID NO:15)
ccggtaccatctgtaccctctacatctttatcaggttatattcctgcaaatacaacaatt
ccttttggtggtgcatacaatattcctttagtatcaggtcctgatatacccattaatata
actgaccaagctccttcattaattcctatagttccagggtctccacaatatacaattatt
gctgatgcaggtgacttttatttacatcctagttattacatgttacgaaaacgacgtaaa
cgtttaccatatttttttcagatgtctctttggctgccTAG (SEQ ID NO:11)
         primer D   <gtctacagagaaaccgacggatcTCTAGACCTCCC<
                         (SEQ ID NO:16)          Bgl II
```

Figure 1

```
ATG CGA CAC AAA CGT TCT GCA AAA CGC ACA AAA CGT GCA TCG GCT ACC CAA CTT
 M   R   H   K   R   S   A   K   R   T   K   R   A   S   A   T   Q   L
 1                                      10

TAT AAA ACA TGC AAA CAG GCA GGT ACA TGT CCA CCT GAC ATT ATA CCT AAG GTT
 Y   K   T   C   K   Q   A   G   T   C   P   P   D   I   I   P   K   V
         20                              30

GAA GGC AAA ACT ATT GCT GAT CAA ATA TTA CAA TAT GGA AGT ATG GGT GTA TTT
 E   G   K   T   I   A   D   Q   I   L   Q   Y   G   S   M   G   V   F
             40                                  50
                                                      Not I,   Sac I  Xho I
TTT GGT GGG TTA GGA ATT GGA ACA GGG TCG GGT ACA GGC GGC CGC GAG CTC GAG
 F   G   G   L   G   I   G   T   G   S   G   T   G   G   R   E   L   E
                     60                                  69  70      72

GGT TAT ATT CCT GCA AAT ACA ACA ATT CCT TTT GGT GGT GCA TAC AAT ATT CCT
 G   Y   I   P   A   N   T   T   I   P   F   G   G   A   Y   N   I   P
                             80                                      90

TTA GTA TCA GGT CCT GAT ATA CCC ATT AAT ATA ACT GAC CAA GCT CCT TCA TTA
 L   V   S   G   P   D   I   P   I   N   I   T   D   Q   A   P   S   L
                                 100

ATT CCT ATA GTT CCA GGG TCT CCA CAA TAT ACA ATT ATT GCT GAT GCA GGT GAC
 I   P   I   V   P   G   S   P   Q   Y   T   I   I   A   D   A   G   D
     110                                 120

TTT TAT TTA CAT CCT AGT TAT TAC ATG TTA CGA AAA CGA CGT AAA CGT TTA CCA
 F   Y   L   H   P   S   Y   Y   M   L   R   K   R   R   K   R   L   P
             130                                 140

TAT TTT TTT TCA GAT GTC TCT TTG GCT GCC TAG (SEQ ID NO:12)
 Y   F   F   S   D   V   S   L   A   A       (SEQ ID NO:13)
                 150                 154
```

| BETA-GALACTOSIDASE ACTIVITIES OF P4R5 CELL LYSATES TRANSFECTED WITH THE LISTED PLASMID CONSTRUCTS AND EVALUATED USTING THE GALACTOSTAR® ASSAY ||
|---|---|
| SAMPLE | BETA-GALACTOSIDASE RELATIVE LIGHT UNITS |
| V1Jp-L2cTot | 229.44 |
| pD5 Tat (POSITIVE CONTROL) | 196.48 |
| MOCK TRANSFECTION (NEGATIVE CONTROL) | 0.40 |

FIG.4

SEQUENCE LISTING

<160> NUMBER OF SEQ IDS NOS: 16

<210> SEQ ID NO 1
<211> LENGTH: 27
<212> TYPE: DNA
<213> ORGANISM: Artificial Sequence
<220> FEATURE:
<223> OTHER INFORMATION: PCR primer

<400> SEQUENCE: 1 cttcccccccg ggcacaaaac aaaatgc                                27

<210> SEQ ID NO 2
<211> LENGTH: 30
<212> TYPE: DNA
<213> ORGANISM: Artificial Sequence
<220> FEATURE:
<223> OTHER INFORMATION: PCR primer

<400> SEQUENCE: 2
ctcgagctcg cggccgcctg tacccgaccc                              30

<210> SEQ ID NO 3
<211> LENGTH: 39
<212> TYPE: DNA
<213> ORGANISM: Artificial Sequence
<220> FEATURE:
<223> OTHER INFORMATION: PCR primer

<400> SEQUENCE: 3
gcggccgcga gctcgagggt tatattcctg caaatacaa                    39

<210> SEQ ID NO 4
<211> LENGTH: 35
<212> TYPE: DNA
<213> ORGANISM: Artificial Sequence
<220> FEATURE:
<223> OTHER INFORMATION: PCR primer

<400> SEQUENCE: 4
ccctccagat ctctaggcag ccaaagagac atctg                        35

<210> SEQ ID NO 5
<211> LENGTH: 46
<212> TYPE: DNA
<213> ORGANISM: Artificial Sequence
<220> FEATURE:
<223> OTHER INFORMATION: PCR primer

<400> SEQUENCE: 5
tcccccggga gatctgccac catgcgacac aaacgttctg caaaac            46

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ggcagccaaa gagacatctg                                         20

<210> SEQ ID NO 7
<211> LENGTH: 42

```
<212> TYPE: DNA
<213> ORGANISM: Artificial Sequence
<220> FEATURE:
<223> OTHER INFORMATION: PCR primer

<400> SEQUENCE: 7
cagatgtctc tttggctgcc atggagccag tagatcctag ac                         42

<210> SEQ ID NO 8
<211> LENGTH: 31
<212> TYPE: DNA
<213> ORGANISM: Artificial Sequence
<220> FEATURE:
<223> OTHER INFORMATION: PCR primer

<400> SEQUENCE: 8
ctcgtaagat ctctattcct tcgggcctgt c                                     31

<210> SEQ ID NO 9
<211> LENGTH: 240
<212> TYPE: DNA
<213> ORGANISM: Human

<400> SEQUENCE: 9
atgcgacaca acgttctgc aaaacgcaca aaacgtgcat cggctaccca actttataaa        60
acatgcaaac aggcaggtac atgtccacct gacattatac ctaaggttga aggcaaaact      120
attgctgatc aaatattaca atatggaagt atggtgtat tttttggtgg gttaggaatt       180
ggaacagggt cgggtacagg cggacgcact gggtatattc cattgggaac aaggcctccc     240

<210> SEQ ID NO 10
<211> LENGTH: 900
<212> TYPE: DNA
<213> ORGANISM: Human

<400> SEQUENCE: 10
acagctacag atacacttgc tcctgtaaga cccccttaa cagtagatcc tgtgggccct       60
tctgatcctt ctatagtttc tttagtggaa gaaactagtt ttattgatgc tggtgcacca     120
acatctgtac cttccatccc cccagatgta tcaggattta gtattactac ttcaactgat     180
accacacctg ctatattaga tattaataat actgttacta ctgttactac acataataat     240
cccactttca ctgacccatc tgtattgcag cctccaacac ctgcagaaac tggagggcat     300
tttacacttt catcatccac tattagtaca cataattatg aagaaattcc tatggataca     360
tttattgtta gcacaaaccc taacacagta actagtagca cacccatacc agggtctcgc     420
ccagtggcac gcctaggatt atatagtcgc acaacacaac aagttaaagt tgtagaccct     480
gcttttgtaa ccactcccac taaacttatt acatatgata atcctgcata tgaaggtata     540
gatgtggata atacattata ttttcctagt aatgataata gtattaatat agctccagat     600
cctgactttt tggatatagt tgctttacat aggccagcat taacctctag gcgtactggc     660
attaggtaca gtagaattgg taataaacaa acactacgta ctcgtagtgg aaaatctata     720
ggtgctaagg tacattatta ttatgatttg agtactattg atcctgcaga agaaatagaa     780
ttacaaacta taacaccttc tacatatact accacttcac atgcagcctc acctacttct     840
attaataatg gcttatatga tatttatgca gatgactta ttacagatac ttctacaacc     900

<210> SEQ ID NO 11
<211> LENGTH: 282
<212> TYPE: DNA
```

-continued

<213> ORGANISM: Human

<400> SEQUENCE: 11

```
ccggtaccat ctgtaccctc tacatcttta tcaggttata ttcctgcaaa tacaacaatt      60
ccttttggtg gtgcatacaa tattccttta gtatcaggtc ctgatatacc cattaatata     120
actgaccaag ctccttcatt aattcctata gttccagggt ctccacaata tacaattatt     180
gctgatgcag gtgactttta tttacatcct agtattaca tgttacgaaa acgacgtaaa      240
cgtttaccat attttttttc agatgtctct ttggctgcct ag                        282
```

<210> SEQ ID NO 12
<211> LENGTH: 465
<212> TYPE: DNA
<213> ORGANISM: Human

<400> SEQUENCE: 12

```
atgcgacaca acgttctgc aaaacgcaca aacgtgcat cggctaccca actttataaa       60
acatgcaaac aggcaggtac atgtccacct gacattatac ctaaggttga aggcaaaact    120
attgctgatc aaatattaca atatggaagt atgggtgtat ttttggtgg gttaggaatt    180
ggaacagggt cgggtacagg cggccgcgag ctcgagggtt atattcctgc aaatacaaca   240
attccttttg gtggtgcata caatattcct ttagtatcag gtcctgatat acccattaat   300
ataactgacc aagctccttc attaattcct atagttccag gtctccaca atatacaatt   360
attgctgatg caggtgactt ttatttacat cctagttatt acatgttacg aaaacgacgt   420
aaacgtttac catattttttt ttcagatgtc tctttggctg cctag                  465
```

<210> SEQ ID NO 13
<211> LENGTH: 154
<212> TYPE: PRT
<213> ORGANISM: Human

<400> SEQUENCE: 13

```
Met Arg His Lys Arg Ser Ala Lys Arg Thr Lys Arg Ala Ser Ala Thr
  1               5                  10                  15

Gln Leu Tyr Lys Thr Cys Lys Gln Ala Gly Thr Cys Pro Pro Asp Ile
             20                  25                  30

Ile Pro Lys Val Glu Gly Lys Thr Ile Ala Asp Gln Ile Leu Gln Tyr
         35                  40                  45

Gly Ser Met Gly Val Phe Phe Gly Gly Leu Gly Ile Gly Thr Gly Ser
     50                  55                  60

Gly Thr Gly Gly Arg Glu Leu Glu Gly Tyr Ile Pro Ala Asn Thr Thr
 65                  70                  75                  80

Ile Pro Phe Gly Gly Ala Tyr Asn Ile Pro Leu Val Ser Gly Pro Asp
                 85                  90                  95

Ile Pro Ile Asn Ile Thr Asp Gln Ala Pro Ser Leu Ile Pro Ile Val
            100                 105                 110

Pro Gly Ser Pro Gln Tyr Thr Ile Ile Ala Asp Ala Gly Asp Phe Tyr
        115                 120                 125

Leu His Pro Ser Tyr Tyr Met Leu Arg Lys Arg Arg Lys Arg Leu Pro
    130                 135                 140

Tyr Phe Phe Ser Asp Val Ser Leu Ala Ala
145                 150
```

<210> SEQ ID NO 14
<211> LENGTH: 30

```
<212> TYPE: DNA
<213> ORGANISM: Artificial Sequence
<220> FEATURE:
<223> OTHER INFORMATION: PCR Primer

<400> SEQUENCE: 14
cccagcccat gtccgccggc gctcgagctc                                    30

<210> SEQ ID NO 15
<211> LENGTH: 40
<212> TYPE: DNA
<213> ORGANISM: Artificial Sequence
<220> FEATURE:
<223> OTHER INFORMATION: PCR Primer

<400> SEQUENCE: 15
gcggccgcga gctcgagggt tatattcctg caaatacaac                         40

<210> SEQ ID NO 16
<211> LENGTH: 35
<212> TYPE: DNA
<213> ORGANISM: Artificial Sequence
<220> FEATURE:
<223> OTHER INFORMATION: PCR Primer

<400> SEQUENCE: 16
gtctacagag aaaccgacgg atctctagac ctccc                              35
```

PROTEIN DELIVERY SYSTEM USING HUMAN PAPILLOMAVIRUS VIRUS-LIKE PARTICLES

CROSS-REFERENCE TO RELATED APPLICATIONS

This application is a 371 of PCT/US99/17931, filed Aug. 10, 1999, which claims the benefit of U.S. provisional application 60/096,638, filed Aug. 14, 1998, which are hereby incorporated by reference.

FIELD OF THE INVENTION

This invention is related to a method of delivering protein to a cell by fusing it to a modified papillomavirus L2 protein, and expressing the fused protein in a virus-like particle. The invention is also directed to modified genes encoding the proteins, the modified virus-like particles and host cells containing the virus-like particles.

BACKGROUND OF THE INVENTION

Human Papillomaviruses (HPVs) infect the genital tract and have been associated with various cancers and other diseases. Recombinantly produced L1 protein and L1+L2 protein can self-assemble to form virus-like particles (VLPs). These VLPs are immunogenic, and may be the basis of a vaccine.

Currently, however there is no known prophylactic vaccine or ideal therapeutic treatment of disease caused by HPV. An immune response to other HPV proteins co-delivered within the context of VLPs such as HPV early proteins or genes may enhance the protective effect of a vaccine. Recently, a paper by Greenstone et al described VLPs in which the L2 protein was modified to create a fusion protein between full length L2 and HPV E2 or E7. (Greenstone et al, 1998 *Proc. Natl. Acad. Sci. USA* 95:1800–1805.) The fusion proteins co-assembled with L1 into VLPs which appeared indistinguishable morphologically from L1 VLPs and in their ability to elicit neutralizing antibodies. Furthermore, in tumor challenge models, mice vaccinated with chimeric L1+L2: E7 fusion VLPs were found to protect mice from E7-expressing tumors.

However, there are potential problems associated with the use of a full-length L2 as a fusion partner. First, due to size retraints, an entire L2 as a fusion partner has a limited capacity to accept large fusion proteins. For instance, fusion of E1 with intact L2 of CRPV leads to morphologically aberrant VLPs. Furthermore, expression of a full-length L2 will most likely affect the activity of enzymatically active proteins and therefore may limit its usefulness to deliver functional proteins into a cell. The minimal sequence requirements of L2 enabling coassembly with L1 into VLPs are unknown and the ability to delete significant portions of L2 while retaining the capacity to assemble with L1 is also unknown.

It would be desirable to provide a minimal L2 fusion protein which still retains the protein delivery function of a full-length L2, yet can deliver larger and functionally-active proteins.

DESCRIPTION OF THE INVENTION

This invention is directed to a method of delivering a peptide or protein to a cell comprising the steps of: a) fusing a nucleic acid sequence encoding the peptide or protein to be delivered to a modified papillomavirus (PV) L2 gene to create a fusion protein gene, wherein the L2 gene is less than full-length and comprises at least the coding sequences for the amino-terminal 69 amino acids and the carboxy-terminal 84 amino acids (aa) of L2; b) expressing the fusion protein gene in a host cell to obtain a fusion protein; c) contacting the fusion protein with PV L1 protein under conditions wherein the fusion protein and the L1 protein spontaneously combine to form a virus-like particle (VLP); and d) delivering the VLP to a cell.

This invention also relates to nucleic acids encoding a fusion protein comprising a less than full-length L2 protein fused to a gene encoding a peptide or protein of interest, and to these fusion proteins. In particular, this invention is related to L2 fusion proteins which comprise less than a full-length L2, and comprise at least the amino terminal 69 amino acids and the carboxy terminal 84 amino acids of L2. Additionally, this invention relates to the virus-like particles (VLPs) which contain the fusion protein, and to cellular hosts containing these VLPs.

DESCRIPTION OF THE DRAWINGS

FIG. 1 shows the assembly of the minimal L2 DNA construct from native HPV16 L2. The coding sequence of HPV16 L2, shown in lower case italics, served as template for PCR amplifications. The initiator and terminator codons are in uppercase. Sense primers, I and A, are shown above the template; anti-sense primers, C and D, below. New sequence information, introduced by PCR amplification are shown in uppercase. The complimentary sequences in primers A and C are underscored.

FIG. 3 is a Western blot of immunoprecipitated yeast lysates, showing co-immunoprecipitation of L2-E chimeric proteins with HPV16 L1 VLP-specific Mab H16: V5. The left panel shows anti-E1 stained immunoblot of minimal L2: E1 fusion (mL2: E1) clones E1-121 to E1-124, mL2: E2 sample E2-23 and no lysate samples are specificity controls. The middle panel shows anti-E7 stained immunoblot of minimal L2: E7 fusion (mL2: E7) clones E7-125 to E7-127 and E7-31; mL2: E2 sample E2-23 and no lysate samples are specificity controls. The right panelshows anti-E2 stained immunoblot of mL2: E2 fusion clones E2-33 a, E2-33 b; sample E2-33 b is also shown with no H16: V5 capture antibody as a control and YP3#1 no E protein control is shown as mL2 vector.

DETAILED DESCRIPTION OF THE INVENTION

The method of this invention can be used with virtually any papillomavirus strain. In preferred embodiments, the HPV is one of the strains which is associated with genital warts and/or genital cancers, and in particular may be selected from the group consisting of: HPV6 a, HPV6 b, HPV11, HPV16, HPV18, HPV31, HPV33, HPV35, HPV42, HPV43, HPV44, HPV45, HPV51, HPV52, and HPV56.

Wild-type virus-like particles are predominantly made of L1 protein, although they contain a minor amount of L2 protein. In accordance with this invention, the VLPs have been modified so that they still contain wild-type L1 protein, but now contain a deleted L2-fusion protein instead of wild-type L2. The L2 segment of the fusion protein is substantially less than the full length L2 protein; it contains peptide domains from the amino terminus and from the carboxyl terminus which are necessary for association with L1 proteins and incorporation into VLPs, at the least, for HPV type 16, the coding sequences for the amino-terminal 69 amino acids and the carboxy-terminal 84 amino acids (aa) of L2. The L2 sequence may be larger than this, as long as it is less than wild-type. Preferably the total amount of L2 amino acids present is less than about 60% of wild type, more preferably less than about 50% of wild-type, and even more preferably less than about 35% of wild type. This modified L2 will be referred to throughout the specification and claims as a "minimal L2" gene and protein.

Virtually any protein or peptide can be fused to the minimal L2 protein to make the fusion protein. HPV proteins which are normally not part of the VLP are preferred if the goal is to make a VLP which induces an increased immune response as compared to a wild-type VLP. For this application, these proteins include but are not restricted to HPV: E1, E2, E3, E4, E5, E6, and/or E7, HIV TAT and/or beta lactamase. Particularly preferred proteins are E1, E2, and E7. These fusion proteins and the nucleic acids encoding them make up another aspect of this invention.

One of the advantages of this invention is that the fusion partner may be a large protein. For example, the fusion partner may be over 50 kD, over 60 kD and even over 70 kD. This increased size allows for the introduction of most known proteins, and makes this delivery system particularly useful not only for HPV-related proteins as described above, but also for proteins which are not associated treatment of with HPV disease.

Thus, this invention includes methods of using a modified VLP as a generalized transporter, directing the delivery of virtually any desired protein or peptide into cells. In one embodiment, reporter or regulatory proteins are delivered to cells as a measure of VLP uptake by cells. As an example of fusion candidates which is by no means limiting, is the regulatory protein of HIV known as TAT. Fusions of TAT to the minimal L2 have been shown to retain protein function as well as form VLPs with L1. This is useful in establishing neutralization assays.

The fusion protein and L1 protein may be made simultaneously by transforming a selected host cell with genes encoding the proteins under conditions which allow expression of the two genes. General techniques, the genes for L1 s and L2, and methods for recombinant expression of L1 and L2 proteins are known in the art, and may be used. Preferred host cells include yeast, insect cells, mammalian cells and *E. coli*.

Under one preferred embodiment of this invention, yeast are transformed with plasmid DNA containing the genes encoding L1 and the L2 fusion under control of known yeast promoters, such as the yeast Gal 1 and Gal 10 promoters. Expression of each gene product is induced by addition of galactose to the growth media, and the VLPs are isolated from the induced cell lysates.

Alternatively, the one set of host cells may be transformed to express only L1 protein, and a second set of host cells may be transformed to express the L2 fusion protein of this invention. The respective proteins are harvested, optionally subjected to a purification step, and are brought into contact so that VLPs containing the fusion protein are formed.

The modified VLPs make up yet another aspect of this invention. These VLPs may be administered as a vaccine, or as part of a therapeutic regimen. Therapeutic or diagnostic compositions of the invention are administered to an individual in amounts sufficient to treat or diagnose PV infections. The effective amount may vary according to a variety of factors such as the individual's condition, weight, gender and age. Other factors include the mode of administration. Generally, the compositions will be administered in dosages ranging from about 1 mcg to about 1 mg.

The pharmaceutical compositions may be provided to the individual by a variety of routes such as subcutaneously, topically, orally, mucosally, intravenously and intramuscularly.

The vaccines of the invention comprise DNA, RNA or proteins encoded by the DNA that contain the amino-terminal and carboxyl-terminal portions of L2 which permit the incorporation of proteins fused to it to be incorporated into VLPs. Such vaccines are also safe enough to be administered without danger of clinical infection, do not have toxic side effects, can be administered by an effective route, are stable, and are compatible with vaccine carriers.

The vaccines may be administered by a variety of routes, such as orally, parenterally, subcutaneously, mucosally, intravenously or intramuscularly. The dosage administered may vary with the condition, sex, weight, and age of the individual; the route of administration; and the type of PV of the vaccine. The vaccine may be used in dosage forms such as capsules, suspensions, elixirs, or liquid solutions. The vaccine may be formulated with an immunologically acceptable carriers or adjuvants, or other excipients.

The vaccines are administered in therapeutically effective amounts, that is, in amounts sufficient to generate a immunologically protective response. The therapeutically effective amount may vary according to the type of PV. The vaccine may be administered in single or multiple doses.

The purified proteins of the present invention may be used in the formulation of immunogenic compositions. Such compositions, when introduced into a suitable host, are capable of inducing an immune response in the host.

The following non-limiting Examples are presented to better illustrate the invention.

EXAMPLE 1

Construction of the Modified L2 Gene

The modified HPV16 L2 gene was constructed from the coding sequences for the amino-terminal 69 amino acids and the carboxy-terminal 84 amino acids (aa) of HPV16 L2 which were fused in frame by a synthetic polylinker that introduced unique Not I, Sac I, and Xho I restriction endonuclease recognition sites and resulted in the insertion of one glutamic acid residue and the mutation of a serine residue to glutamic acid. (FIG. 1).

PCR primers (Midland Certified Reagents; Midland, Tex.) were designed to amplify L2 sequences from the native L2 gene contained within the vector, pGal110 (Hofmann, K, et al 1995 *Virology* 209:506–518) into which the genes encoding HPV16 L1+L2 were inserted. (See FIG. 1).

Primers I (5'-CTT CCC CCC GGG CAC AAA ACA AAA TGC-3'; SEQ. ID. NO. 1) and C (5'-CTC GAG CTC GCG GCC GCC TGT ACC CGA CCC-3'; SEQ. ID. NO. 2) amplified a 265 base pair (bp) sequence encoding the amino-terminal 69 aa and 23 bp of upstream untranslated sequence including a Sma I restriction enzyme site. Primer C modified and extended the L2 amino terminal-encoding region and appended Not I, Sac I and Xho I restriction enzyme sites downstream of the L2-encoding sequences.

Primers A (5'-GCG GCC GCG AGC TCG AGG GTT ATA TTC CTG CAA ATA CAA-3'; SEQ. ID. NO. 3), C and D (5'-CCC TCC AGA TCT CTA GGC AGC CAA AGA GAC ATC TG-3' SEQ. ID. NO. 4) amplified a 285 bp sequence encoding the carboxy-terminal 84 aa of L2 plus 6 bp which added a Bgl II restriction enzyme site. Primer A also appended a 17 bp sequence containing Not I, Sac I, and Xho I sites upstream of the L2-encoding sequence.

The minimal L2 expression construction was assembled through complementary sequences added by primers A and C. The isolated DNA products of the I/C and A/D amplification reactions above were both used in a PCR reaction which included the I and D primers. To facilitate the joining of the fragments through their 17 bp complementary sequence, three PCR cycles were performed with the annealing temperature at 37° C., followed by 15 cycles with the annealing temperature of 57° C. The resulting amplification product was blunt-end ligated into pcrScript (Stratagene, LaJolla, Calif.) and transformed into XL-1 Blue MRF' cells (Stratagene). Positive clones were identified by PCR using primers I and D, and confirmed by restriction digest analysis. The construction was then verified by automated sequence analysis (Perkin Elmer, Inc., Foster City, Calif.).

Figure 2:
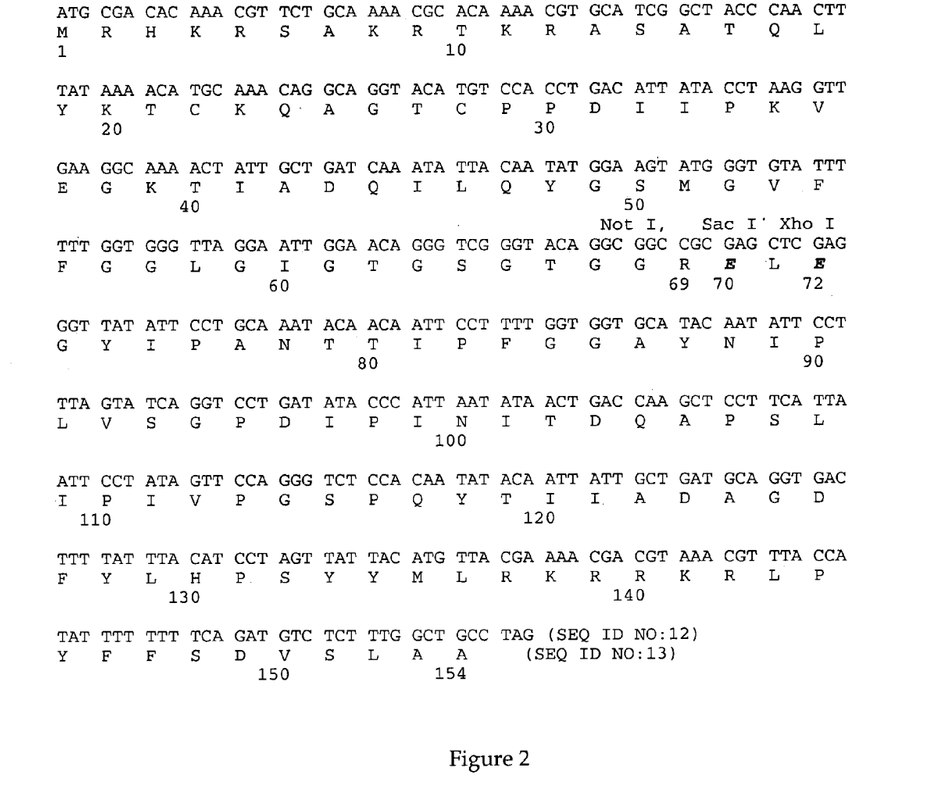
FIG. 2 is the amino acid translation of the HPV 16 Minimal L2 Gene. Amino acid changes resulting from the introduction of the polylinker containing unique restriction sites Not I, Sac I, and Xho I are indicated by italics. Amino acids 1–69 are contributed from the amino terminus of L2. A glutamic acid residue is added at position 70. Amino acids 71–154 are contributed from the carboxyl terminus of L2. At position 72, a glutamic acid residue replaces a serine found in the full-length wildtype L2.

Plasmid DNA from an appropriate isolate was then digested with Sma I and Bgl II; a fragment of approximately 0.5 kilobase pairs (kb) was gel purified and ligated with the 14 kb Sma I and Bgl II vector fragment of pGAL110 into which the HPV16 L1 gene was inserted adjacent to the GAL 1 promoter. Competent DH5 *E. coli* cells (Gibco BRL, Rockville, Md.) were transformed with the ligation mixture and transformants selected on LB ampicillin plates (Remel, Lenexa, Kans.). Clones were initially screened by PCR in which primers D and I were used to amplify portions of L2. Sequencing of candidate clone YP3#1 verified the sequence to be that as shown in FIG. 2.

YP3#1 was then employed as the backbone construct into which genes encoding HPV16 E1, E2, E7 or Tat open reading frames were inserted.

EXAMPLE 2

Insertion of HPV E Protein- and Tat-Encoding Genes

The gene encoding HPV16 E2 was obtained by PCR amplification of a HPV16 positive clinical sample which was then inserted directly into the subcloning vector pCRII (Stratagene) and sequence verified as above. The E2 gene sequence was then modified in the following manner:

1) In-frame Xho I, Nae I, Not 1-containing DNA sequences were added to the amino terminal portion of E2. Additionally, Not I, Nae I, and Xho I-containing sequences were added to the carboxyl-terminal portion of E2 to facilitate insertion within E2 at the Not I, Xho I sites.

2) The DNA sequences were altered by PCR mutagenesis to encode alanine residues encode at residues glutamic acid 39 and isoleucine 73. This was designed to inactivate E2 protein function.

The modified HPV16 E2 gene described above was digested with Not I, Xho I and ligated with similarly digested YP3#1 vector. Transformants containing the properly-inserted E2 sequences were selected by PCR sequence verified and designated YP3-E2.

A similar approach was employed for inserting the genes encoding HPV16 E1, HPV16 E7 and HIV Tat (creating YP3-E 1, YP3-E7 and YP3-Tat, respectively). The construct in which Tat was inserted at the carboxy terminus of minimal L2 was designated as YP3-cTat. For E1, glycine 482 was altered to aspartic acid; for E7, cysteine 24 and glutamic acid 26 were both changed to glycine to inactivate protein function. The resultant constructions were then used to transform yeast.

EXAMPLE 3

Identification and Growth of Yeast Expressing Chimeric VLPs

Plasmid DNA of YP3#1 and derivatives described above were used to transform *Saccharomyces cerevisiae* (MATa, leu2-04, prb1:: HIS3, mnn9:: URA3, cir°) by the spheroplast method (Hinnen et al., 1978, *Proc. Natl. Acad. Sci. USA* 75:1929–1933). Transformed spheroplasts were plated onto selective (leucine minus) medium (Remel, Lenexa, Kans.). Clones were isolated through two rounds of single colony selection. Small liquid cultures of candidate clones were grown to high cell density in medium containing galactose. Crude extracts were prepared by vigorous agitation with glass beads followed by centrifugation. The clarified extracts were analyzed for expression of L1, the L2 component, and VLPs by various methods including SDS PAGE, ELISA, immunoblotting, and EIA, using monoclonal antibodies or monospecific polyclonal antisera that recognize L1, or L2, or the amino or carboxy termini of L2, or L1 VLPs, or E1, or E2, or E7, or any other protein or peptide fused to the modified L2. Clones which expressed the L2 component and formed VLPs were selected for further characterization. One-liter or 16-liter cultures of selected clones were grown in galactose containing medium for large-scale preparation of chimeric VLPs.

EXAMPLE 4

Purification of HPV Type 16 L1/L2$_{mini}$/E2 Chimeric VLPs

Cell pellets from a 16-liter fermentation of *S. cerivesiae* were stored frozen at −70° C. Frozen cells "Breaking Buffer" (200 mM MOPS, pH 7, 1 mM CaCl$_2$) was added to give approximately 20% (w/v) slurry. BENZONASE® (Nycomed Pharma) was added to 750 units/g wet cell weight. The cell slurry was broken at a pressure of approximately 19,000 psi by 5 passes in a M110-Y Microfluidizer (Microfluidics Corp., Newton, Mass.). The cell lysate was clarified by microfiltration through a 0.65 micron pore size hollow-fiber cartridge and then diafiltered with three volumes of 0.25 M sodium citrate, 0.2 M MOPS, pH 7.0. Permeate was loaded onto a POROS® 50 HS resin (Perseptive Biosystems, Cambridge, Mass.) equilibrated in 200 mM MOPS, pH 7, 250 mM sodium citrate. The column was washed with 50 mM MOPS, 0.5 M NaCl, 5 mM sodium phosphate, pH 7 and eluted with a linear gradient from 0.5 to 1.5 M NaCl in the same buffer. Column fractions were analyzed by immunoblotting and SDS-PAGE with colloidal Coomassie detection.

The 50 HS pool was filtered through a 0.22 mm filter and applied to a ceramic hydroxyapatite (HA) Type II (Bio-Rad) column. The column was washed with 50 mM MOPS, pH 7, 1.25 M NaCl, 5 mM sodium phosphate and eluted with a linear gradient from 5 to 200 mM sodium phosphate, pH 7 in 1.25 M NaCl. Fractions were analyzed by Western blot and SDS-PAGE. Fractions showing comparable purity and enrichment of L1 protein were pooled. The pooled fractions were filtered aseptically through a 0.22 mm membrane and submitted for electron microscopy.

EXAMPLE 5

Detection of VLPs by Electron Microscopy

Transmission electron microscopy was performed by EMBS (Elkridge, Md.). Appropriately diluted samples were placed on a 300 mesh carbon-coated copper grid and allowed to air dry. Grids were stained with phosphotungstic acid. All microscopy was performed using a JEOL 1200 EX transmission electron microscope. The micrographs generated had a final magnification of 138,000×. Electron microscopy confirmed the presence of intact VLP particles with a mean diameter of 32 nm. These particles were indistinguishable morphologically from yeast-expressed L1 or L1+L2 particles. Confirmation of the presence of L2 fusions within the VLPs was demonstrated by immunoblotting analysis of process fractions (See Example 6).

EXAMPLE 6

Co-Immunoprecipitation of L2 Fusion Proteins with L1 Specific Anti-VLP Antibodies To show that the L2 fusions were an integral component of the VLPs, VLPs were captured by an HPV16 L1 VLP-specific monoclonal antibody (mAb) H16: V5 (Wang, D. et al. 1997 *J. General Virology,* 78: 2209–2215), washed extensively and the retained products detected by immunoblotting. In brief, magnetic beads precoated with sheep anti-mouse IgG (Dynabeads M-280; Dynal, Oslo) were washed with TMOPS buffer (0.05M MOPS, pH 7.0, 0.4M NaCl, 0.1% Tween-80) containing 5% non-fat dry milk. The washed beads were incubated overnight at 4° C. with H16: V5 mAb in the same solution. Unbound mAb was removed by washing with TMOPS. Beads were then incubated with control or VLP-containing crude yeast extracts (see Example 3) or partially-purified VLP preparations (see Example 4). Extracts containing 100–400 µg total protein were diluted with 0.2 MOPS, pH 7.0, 2 mM MgCl$_2$ and incubated with beads for 4 hours at 4° C. Beads were then washed extensively with TMOPS; bound proteins were recovered by heating the beads at 95° C. in Laemmli sample buffer, resolved by SDS-PAGE and identified by immunoblotting.

Figure 3:
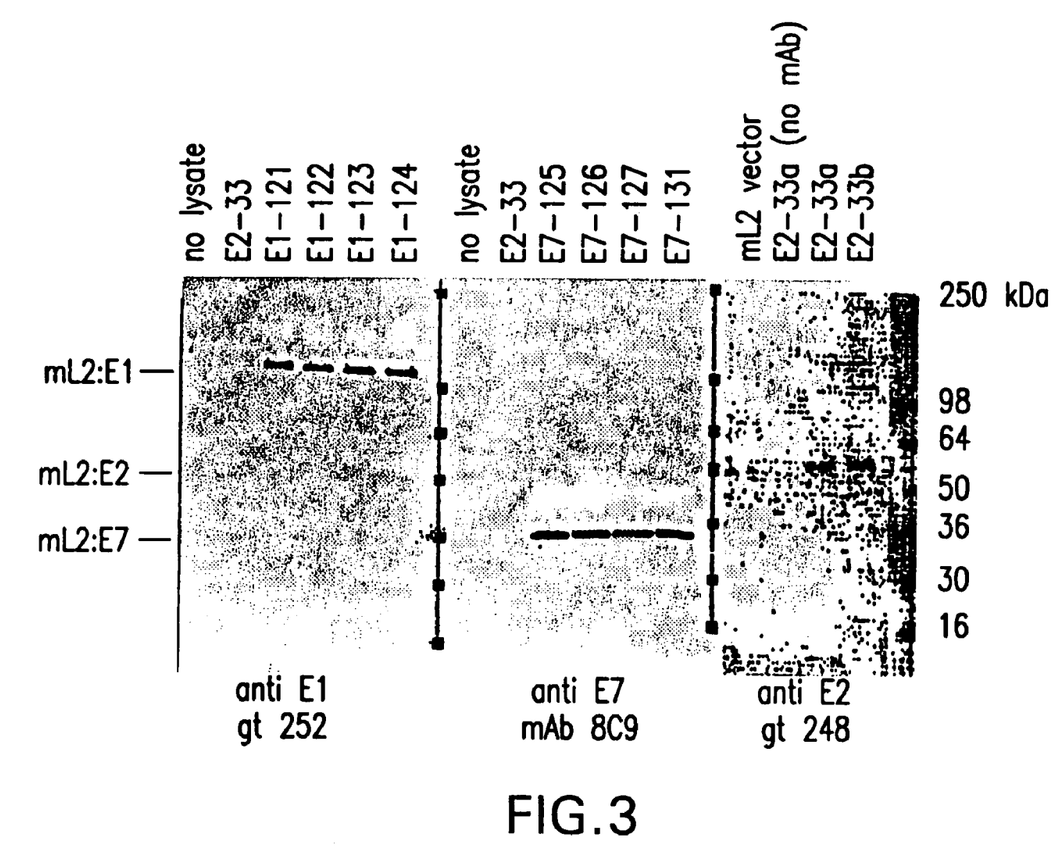

Identification of the L2 fusion protein was performed with antibodies that recognize the L2 portion of the protein and by antibodies that recognize the protein of interest fused to L2, for example E1, E2, or E7. In addition to the inclusion of control yeast extracts, other controls included 1) beads which have not been incubated with H16: V5, and 2) beads which have not been incubated with yeast extract. FIG. 3 shows the immunoblot results of VLPs captured by the H16: V5 Mab and immunoblotted as described above and then stained with anti-E1, anti-E7 or anti-E2 antisera. In each case for multiple isolates, the E-protein: L2 fusions were detected amount the captured, purified VLPs using the appropriate antibody, but not in the absence of lysate or using purified chimeric VLPs containing E-proteins different from the detection antisera.

Coprecipitation of the L2 fusion protein with L1 using a monoclonal antibody specific for L1 VLPs was taken as an indication that the L2 fusion protein was associated with the VLP.

EXAMPLE 7

Demonstration of Tat Activity in Tat/Minimal L2 Fusions in Mammalian Cells

To demonstrate that Tat/L2 fusions retained Tat activity, an expression plasmid was constructed in which DNA encoding the HIV Tat gene was inserted downstream of the minimal L2 gene so that it would be linked to the carboxyl terminus of L2 in the translated product. This DNA cassette was digested with Bgl II and inserted within the Bgl II site of the mammalian expression vector, V1 Jp (Montgomery, D. et al 1993 *DNA & Cell Biol.* 12:777) adjacent to the CMV promoter. The L2/Tat fusion was created by PCR of the minimal L2 (lacking a translational stop signal) using the oligomers 5'-TCC CCC GGG AGA TCT GCC ACC ATG CGA CAC AAA CGT TCT GCA AAA C-3' (primer W; SEQ ID NO:5) and 5'-GGC AGC CAA AGA GAC ATC TG-3' (primer X; SEQ ID NO:6). Oligomers 5'-CAG ATG TCT CTT TGG CTG CCA TGG AGC CAG TAG ATC CTA GAC-3'(primer Y; SEQ ID NO:7) and 5'-CTC GTA AGA TCT CTA TTC CTT CGG GCC TGT C-3'(primer Z; SEQ ID NO:8) were used to amplify the complete Tat open reading frame and to introduce sequence complementarity with L2. The products from both PCR reactions were agarose gel isolated and then combined in a second PCR reaction in which only primers W and Z were added which generated the L2/Tat fusion through overlap of complementary sequences. These primers also appended Bgl II sites which were digested to facilitate insertion within V1 Jp to form V1 Jp-L2 cTat.

Figure 4:
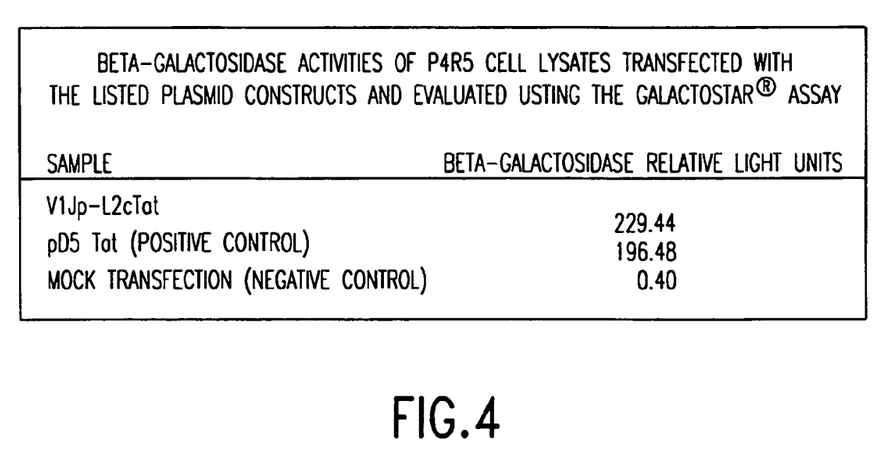
FIG. 4 is a table listing beta galactosidase activities of transiently transfected cell lysates.

Activity of the L2/Tat fusion was determined by transfection of V1 Jp-L2 cTat into P4 R5 cells using a calcium phosphate transfection kit (available from Gibco BRL, Rockville, Md.) performed as recommended by the manufacturer. P4 R5 cells contain an integrated copy of the gene encoding beta galactosidase under control of the HIV LTR. If the introduced Tat gene encodes functionally active Tat, expressed Tat protein will bind the LTR and result in expression of beta galactosidase. Lysates were made of 48 hr post transfection cultures and beta galactosidase activity assessed using Galactostar® reagents (Tropix, Bedford, Miss.). The results are summarized in FIG. 4 which shows that there were similar amounts of beta galactosidase produced in cells transfected with V1 Jp-L 2 cTat as with the unfused positive control pD5-Tat plasmid (235 vs. 175). The no-Tat DNA control had a value of 0.462. Thus, full Tat activity appears to be retained within the L2/Tat fusion.

What is claimed is:

1. A method of delivering a peptide or protein to a cell comprising:
   a) fusing a nucleic acid sequence encoding the peptide or protein to a modified human papillomavirus (HPV) L2 gene to create a fusion protein gene;
   b) expressing the fusion protein gene in a host cell to obtain fusion protein;
   c) contacting the fusion protein with HPV L1 protein under conditions wherein the fusion protein and the L1 protein spontaneously combine to form a virus like particle (VLP); and d) delivering the VLP to the cell;

(i) wherein the modified HPV L2 gene encodes less than about 50% of wild type L2 protein and encodes domains from the amino and the carboxyl termini; and (ii) wherein the HPV L2 gene is from an HPV strain selected from the group consisting of: HPV6a, HPV6b, HPV11, HPV16, HPV18, HPV31, HPV33, HPV35, HPV42, HPV43, HPV44, HPV45, HPV51, HPV52, and HPV56.

2. A HPV virus-like particle (VLP) comprising HPV L1 protein and a fusion protein wherein the fusion protein comprises:

a first protein which is an HPV L2 protein which is less than about 50% of wild type; and a second protein or peptide.

3. A VLP according to claim 2 wherein the HPV L2 protein is from a HPV strain selected from the group consisting of: HPV6 a, HPV6 b, HPV11, HPV16, HPV18, HPV31, HPV33, HPV35, HPV42, HPV43, HPV44, HPV45, HPV51, HPV52, and HPV56.

4. A host cell comprising the VLP of claim 2.

5. A nucleic acid encoding a VLP according to claim 3.

* * * * *